United States Patent
Van Cleve et al.

(10) Patent No.: US 10,928,399 B2
(45) Date of Patent: Feb. 23, 2021

(54) CUSTOMIZABLE INSTRUMENT

(71) Applicant: HYCOR BIOMEDICAL, LLC, Indianapolis, IN (US)

(72) Inventors: Mark David Van Cleve, Long Beach, CA (US); Elaine Grace Taine, Anaheim, CA (US); Stephanie Tuvi Ortega, Huntington Beach, CA (US); Douglas John Canfield, Ludington, MI (US); Taylor Addison Reid, Carlsbad, CA (US); Eunbyul Cho, Carson, CA (US); Jocelyn Lindari Argueta, Long Beach, CA (US)

(73) Assignee: HYCOR Biomedical, LLC, Indianapolis, IN (US)

( * ) Notice: Subject to any disclaimer, the term of this patent is extended or adjusted under 35 U.S.C. 154(b) by 235 days.

(21) Appl. No.: 15/745,397

(22) PCT Filed: Jul. 13, 2016

(86) PCT No.: PCT/US2016/042101
§ 371 (c)(1),
(2) Date: Jan. 16, 2018

(87) PCT Pub. No.: WO2017/011560
PCT Pub. Date: Jan. 19, 2017

(65) Prior Publication Data
US 2019/0101542 A1 Apr. 4, 2019

Related U.S. Application Data

(60) Provisional application No. 62/214,740, filed on Sep. 4, 2015, provisional application No. 62/192,989, filed on Jul. 15, 2015.

(51) Int. Cl.
*C12M 1/34* (2006.01)
*G01N 33/58* (2006.01)
(Continued)

(52) U.S. Cl.
CPC .............. *G01N 33/582* (2013.01); *C12M 1/34* (2013.01); *G01N 21/6428* (2013.01);
(Continued)

(58) Field of Classification Search
CPC ...... G01N 33/582; G01N 33/58; G01N 33/50; G01N 33/48; G01N 21/6428; G01N 21/636; G01N 21/63; G01N 21/62
(Continued)

(56) References Cited

U.S. PATENT DOCUMENTS 5,281,540 A   1/1994 Merkh
5,311,426 A   5/1994 Donohue et al.
(Continued)

FOREIGN PATENT DOCUMENTS

CN      103163294 B    6/2015
EP      0410645 A2     1/1991
(Continued)

OTHER PUBLICATIONS

Extended European Search Report for European Patent Application No. 16825115.5, dated Feb. 18, 2019.
(Continued)

*Primary Examiner* — Christine T Mui
(74) *Attorney, Agent, or Firm* — K&L Gates LLP; Louis C. Cullman; Dennis A. Majewski

(57) ABSTRACT

Methods and apparatus that mix a plurality of individual capture reagents for the diagnostic assays are described herein. In an embodiment, a system for optically analyzing a patient sample includes an automated immunochemistry analyzer storing a plurality of capture reagents and a plurality of paramagnetic particles, a user interface configured to allow a selection of a combination of two or more of the capture reagents, and a logic implementer configured to cause the automated immunochemistry analyzer to (i) mix
(Continued)

together each capture reagent of the combination of two or more of the capture reagents; (ii) bind the mixture of the combination of two or more of the capture reagents to the paramagnetic particles; (iii) bind the patient sample to the bound mixture of the combination of two or more of the capture reagents; and (iv) optically analyze the patient sample.

20 Claims, 9 Drawing Sheets

(51) Int. Cl.
    *G01N 35/00*     (2006.01)
    *G01N 21/64*     (2006.01)
    *C12M 1/00*     (2006.01)
    *B01L 3/00*     (2006.01)
    *G01N 21/75*     (2006.01)
    *G01N 35/04*     (2006.01)

(52) U.S. Cl.
    CPC ......... *G01N 33/58* (2013.01); *G01N 35/0092* (2013.01); *G01N 35/0098* (2013.01); *G01N 35/00871* (2013.01); *B01L 3/00* (2013.01); *C12M 1/00* (2013.01); *G01N 21/75* (2013.01); *G01N 2035/0091* (2013.01); *G01N 2035/00564* (2013.01); *G01N 2035/00881* (2013.01); *G01N 2035/0439* (2013.01); *G01N 2800/24* (2013.01)

(58) Field of Classification Search
    USPC .......................................................... 436/149
    See application file for complete search history.

(56) References Cited

U.S. PATENT DOCUMENTS

| | | | |
|---|---|---|---|
| 5,320,808 A | 6/1994 | Holen et al. | |
| 5,773,296 A | 6/1998 | Montalbano et al. | |
| 5,885,529 A | 3/1999 | Babson et al. | |
| 5,885,530 A | 3/1999 | Babson et al. | |
| 6,498,010 B1 | 12/2002 | Fitzgerald et al. | |
| 6,592,822 B1 | 7/2003 | Chandler | |
| 7,497,997 B2 | 3/2009 | Glezer et al. | |
| 7,858,321 B2 | 12/2010 | Glezer et al. | |
| 8,951,721 B2 | 2/2015 | Pamula et al. | |
| 9,040,288 B2 | 5/2015 | Handique et al. | |
| 2005/0220671 A1 | 10/2005 | Stein et al. | |
| 2008/0241937 A1 | 10/2008 | Wakamiya et al. | |
| 2010/0144055 A1 | 6/2010 | Holzman et al. | |
| 2011/0104010 A1 | 5/2011 | Brown et al. | |
| 2012/0282684 A1 | 11/2012 | Fritchie et al. | |
| 2014/0256588 A1 | 9/2014 | Glezer et al. | |
| 2014/0273277 A1 | 9/2014 | Diamond et al. | |
| 2014/0274784 A1* | 9/2014 | Van Cleve | G01N 33/5434 506/9 |

FOREIGN PATENT DOCUMENTS

| | | |
|---|---|---|
| JP | H01-158354 | 6/1989 |
| JP | 2000-266758 | 9/2000 |
| WO | 1993/003347 A1 | 2/1993 |
| WO | 9800697 | 1/1998 |
| WO | 0237078 | 5/2002 |
| WO | 0242775 | 5/2002 |
| WO | 2003/050539 A1 | 6/2003 |
| WO | 2009/061641 A2 | 5/2009 |
| WO | 2012/054638 A2 | 4/2012 |
| WO | 2014127379 | 8/2014 |
| WO | 2014/145581 A1 | 9/2014 |
| WO | 2016/159960 A1 | 10/2016 |
| WO | 2017/011560 A1 | 1/2017 |
| WO | 2017/015662 A1 | 1/2017 |

OTHER PUBLICATIONS

Office Action and Search Report in related Chinese Application Serial No. 201680041555.8 dated Jun. 24, 2019 and English translation of same.
Office Action in related Chinese Application Serial No. 201680042979.6 dated Apr. 23, 2019 and English translation of same.
International Search Report for International Patent Application No. PCT/US/2016/042101, dated Sep. 29, 2016.
Written Opinion for International Patent Application No. PCT/US/2016/042101, dated Sep. 29, 2016.
Extended European Search Report for European Patent Application No. 16828686.2, dated Jan. 21, 2019.
International Preliminary Report on Patentability issued in related International Patent Application No. PCT/US2016/043873, dated Jan. 23, 2018.
U.S. Appl. No. 15/746,896, filed Jan. 23, 2018.
Japanese Office Action dated Jan. 8, 2019 for Japanese Patent Application No. 2018-501283 (English translation and original provided).

* cited by examiner

CUSTOMIZABLE INSTRUMENT

CROSS REFERENCE TO RELATED APPLICATIONS

This application is a national phase entry of PCT/US2016/042101, filed Jul. 13, 2016, which claims the benefit of U.S. provisional patent application No. 62/192,989, filed Jul. 15, 2015, and U.S. provisional patent application No. 62/214,740, filed Sep. 4, 2015, the entire disclosures each of which is incorporated herein by reference.

FIELD OF THE DISCLOSURE

The present disclosure relates generally to methods and apparatuses for performing diagnostic assays, and more specifically to methods and apparatus that mix a plurality of individual capture reagents for the diagnostic assays.

BACKGROUND OF THE DISCLOSURE

Many immunochemistry analysis systems require that analyte molecules in a patient's biological sample (e.g. serum or plasma) attach to paramagnetic particles. To bind analyte molecules of interest to the paramagnetic particles, a capture reagent is first bound to the paramagnetic particles, and then the patient sample is bound to the capture reagent. The analyses performed by such systems, however, are relatively slow and inefficient because the systems do not provide the capability for a user to customize a mixture of multiple capture reagents and therefore optimize the analysis of the patient sample for different types of analyte molecules of interest.

SUMMARY OF THE DISCLOSURE

Described herein are methods and apparatus that mix a plurality of individual capture reagents for diagnostic assays so that the analysis of a patient sample can be optimized for different types of analyte molecules of interest.

Thus, disclosed herein is a system for optically analyzing a patient sample for a plurality of allergens, the system comprising: an automated immunochemistry analyzer configured to store a plurality of capture reagents and a plurality of paramagnetic particles; a user interface configured to allow a selection of a combination of two or more capture reagents from the plurality of capture reagents; and a logic implementer configured to cause the automated immunochemistry analyzer to (i) mix together each capture reagent of the combination of two or more capture reagents, (ii) bind the mixture of the combination of two or more capture reagents to the paramagnetic particles, (iii) bind analyte molecules from the patient sample to the bound mixture of the combination of two or more capture reagents, and (iv) optically analyze the bound analyte molecules from the patient sample.

In certain embodiments, the logic implementer is configured to limit the number of capture reagents that the user interface allows for selection. In other embodiments, the logic implementer is configured to limit the number of capture reagents that the user interface allows for selection based on the availability of the capture reagents within the automated immunochemistry analyzer. In yet other embodiments, the logic implementer is configured to adjust the number of capture reagents that the user interface allows for selection as a selection is being made.

In other embodiments, the logic implementer is configured to store a plurality of preprogrammed combinations of two or more capture reagents for selection using the user interface. In yet other embodiments, the plurality of preprogrammed combinations are sorted by type of symptom exhibited by the patient. In other embodiments, the selection of the combination of two or more capture reagents is made by individually selecting each of the capture reagents in the combination. In yet other embodiments, the logic implementer is configured to cause the automated immunochemistry analyzer to perform additional analysis using at least one of the two or more capture reagents if a test using the combination of two or more capture reagents returns a positive result.

Also disclosed herein is a method of optically analyzing a patient sample for a plurality of allergens, the method comprising: selecting a combination of two or more capture reagents from a plurality of selectable capture reagents; adding each capture reagent of the combination of two or more capture reagents to a container containing paramagnetic particles; binding the combination of two or more capture reagents to the paramagnetic particles; binding analyte molecules from the patient sample to the combination of two or more capture reagents; and optically analyzing the bound analyte molecules from the patient sample.

In certain embodiments, the method includes narrowing the number of capture reagents that are available for selection. In other embodiments, selecting from the plurality of selectable capture reagents includes selecting from a plurality of preprogrammed combinations of two or more capture reagents. In yet other embodiments, selecting from the plurality of selectable capture reagents includes individually selecting each capture reagent from the plurality of selectable capture reagents. In yet further embodiments, the method includes performing additional optical analysis using at least one of the two or more capture reagents from the combination if a test using the combination of two or more capture reagents returns a positive result.

Also disclosed herein is a system for optically analyzing a patient sample for a plurality of allergens, the system comprising: a plurality of capture reagents; a plurality of paramagnetic particles; a selection module that allows a selection of a combination of two or more capture reagents from the plurality of capture reagents; a mixing module that (i) mixes together each capture reagent of the combination of two or more capture reagents, (ii) binds the mixture of the combination of two or more capture reagents to the paramagnetic particles, and (iii) binds analyte molecules from the patient sample to the bound mixture of the combination of two or more capture reagents; an analysis module that optically analyzes the bound analyte molecules from the patient sample for one or more positive or negative result; and a reporting module which reports the one or more positive or negative result determined by the analysis module.

In certain embodiments, the system includes an inventory tracking module that stores locations of the plurality of capture reagents. In other embodiments, the inventory tracking module communicates the locations of the plurality of capture reagents to at least one of: (i) the selection module; (ii) the mixing module; and (iii) the analysis module. In yet another embodiment, the system includes an inventory replenishment module that replenishes the plurality of capture reagents.

In other embodiments, the analysis module instructs the mixing module to mix a second combination of two or more capture reagents if a test of the combination of two or more capture reagents returns a positive result. In yet other embodiments, the selection module allows for individual selection of each capture reagent of the combination of two or more capture reagents. In yet other embodiments, the selection module allows for selection of the combination of two or more capture reagents from a plurality of preprogrammed combinations of two or more capture reagents.

BRIEF DESCRIPTION OF THE DRAWINGS

Embodiments of the present disclosure will now be explained in further detail by way of example only with reference to the accompanying figures, in which.

DETAILED DESCRIPTION

Before describing in detail the illustrative system and method of the present disclosure, it should be understood and appreciated herein that the present disclosure relates to methods and apparatus that mix a plurality of individual capture reagents to optimize diagnostic assays for different types of analyte molecules of interest. In general, the system utilizes common paramagnetic particles, for example, magnetic beads or microparticles that are pulled to the wall of a reaction cuvette by magnets during a washing process so that liquid can be aspirated from the cuvette.

In some embodiments, the present systems are not microfluidics systems which may include DNA chips, lab-on-a-chip technology, micro-propulsion, and micro-thermal technologies. In some embodiments, the present systems include immunoanalyzer instruments that can use one or more automated pipettor, reaction rotors, physically picking up and moving samples and reagents, and combinations thereof.

In the beginning of the process, the paramagnetic particles are coated with one or more capture reagent that will eventually bind analyte molecules of interest in the patient's blood sample. After the capture reagents bind to the paramagnetic particles and the cuvettes undergo a washing process, the patient sample, and optionally a diluent if needed, is added to the particles in the reaction cuvette and incubated. This allows analytes of interest in the patient's blood sample to bind to the one or more capture reagent that has in turn been bound to the surface of a paramagnetic particle.

After the patient sample incubation period, another washing process is performed to remove any excess or unbound sample. Then, a conjugate and a luminescent label are added to the cuvette. When added to the cuvette, it can be expected that some portion of the conjugate will bind to the capture reagent/sample complex on the paramagnetic particles after an incubation period. The particles then undergo another wash process to remove any unbound conjugate. Then, a luminescent label is added to the reaction cuvette and incubated for a short period of time to allow the chemiluminescent glow reaction to reach equilibrium. After equilibrium is reached, luminescence and fluorescence readings of the sample can be taken.

Figure 1:
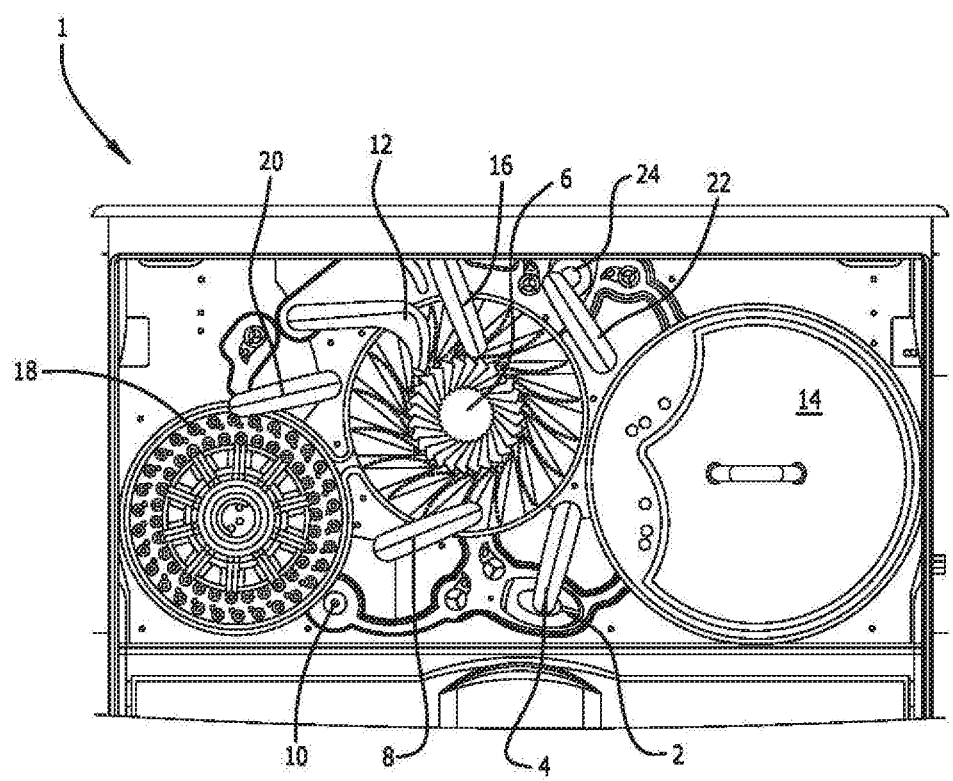
FIG. 1 is a top schematic view of an embodiment of an automated immunochemistry analyzer and reagent system according to the present disclosure.

FIG. 1 illustrates various components of an embodiment of an automated immunochemistry analyzer 1 according to the present disclosure. Automated immunochemistry analyzer 1 can take an analyte sample, create an environment that will allow it to bind to a paramagnetic particle, perform a number of washing steps, and then quantify and normalize the luminescence signal of the analyte sample. This can be accomplished through an automated process that utilizes a vortexer 2, an R1 pipettor 4, a reaction rotor 6, an optics pipettor 8, an optics box 10, a multi rinse pipettor 12, a reagent rotor 14, a single rinse pipettor 16, a sample rotor 18, a sample pipettor 20, an R2 pipettor 22, and a mixed substrate container 24.

To better understand the present disclosure, a sample process will be outlined explaining one possible method the apparatus could utilize to quantify and normalize the luminescence signal of an analyte sample. In an embodiment, automated immunochemistry analyzer 1 begins by first dispensing fluorescently labelled paramagnetic particles, or fluo-beads, into a cuvette located within the reaction rotor 6. The fluo-beads can be initially located in vortexer 2 and transferred to reaction rotor 6 by R1 pipettor 4. R1 pipettor 4 can aspirate a desired quantity of the fluo-bead mixture and transfer the aspirated quantity to reaction rotor 6 where it is injected into the cuvette of reaction rotor 6. Optics pipettor 8 can then aspirate a test sample from the cuvette of reaction rotor 6 and transfer the test sample to optics box 10, where fluorescence and luminescence measurements can be recorded.

The fluorescence and luminescence measurements can be taken directly through the at least partially transparent optics pipette tip. The optics box can include at least one light source and at least one detector. The light source(s) can project light at the optics pipette tip. Detectors can be placed behind the optics pipette tip thereby capturing light traveling through the optics pipette tip and its contents or can be placed at other locations in the optics box that can collect scattered or reflected light. One skilled in the art can envision various configurations.

The initial recording of the fluorescence and luminescence signal can be used as a baseline measurement for the fluorescence signal that can correspond to the initial concentration of fluo-beads in a sample. After recording the measurements, multi rinse pipettor 12 can rinse the cuvettes using a wash buffer.

Next, fluo-beads can be transferred from vortexer 2 to a cuvette in reaction rotor 6 via R1 pipettor 4. R1 pipettor 4 can aspirate one or more capture reagent from the reagent rotor 14 and inject the one or more capture reagent into the cuvette located in reaction rotor 6. After an incubation period, single rinse pipettor 16 can inject a rinse buffer to stop the capture reagent binding reaction with precise timing. A substantial amount of the suspended fluo-bead can then be localized by magnets within the reaction rotor 6 over a period of time. After the magnets have substantially localized the fluo-beads within the cuvette, multi rinse pipettor 12 can aspirate and dispose of a portion of the rinse buffer, leaving a portion of the fluo-beads localized within the cuvette. Multi rinse pipettor 12 can proceed to inject a wash buffer into the cuvette of reaction rotor 6, resuspending the fluo-beads. The fluo-beads can again be localized by the magnets within reaction rotor 6 to be followed by multi rinse pipettor 12 aspirating and discarding a portion of the sample that was not localized from the cuvette in the reaction rotor 6.

A patient sample can be contained in a sample tube in sample rotor 18. The patient sample can further be partially diluted with a sample diluent. At this point, sample pipettor 20 can aspirate a portion of the patient sample and inject the patient sample into the cuvette of reaction rotor 6 to resuspend the fluo-beads. The cuvette containing the patient sample within the reaction rotor 6 can then incubate the patient sample. In one embodiment, the incubation temperature can be about 37 degrees Celsius+/−about 0.2 degree Celsius while the incubation time can be about 37.75 minutes+/−about 2 minutes. After incubation, multi rinse pipettor 12 can inject the rinse buffer to again resuspend the fluo-beads. Another localization process is performed by reaction rotor 6 by allowing the fluo-beads to substantially collect within the cuvette near the magnets in reaction rotor 6. After the localization of the fluo-beads, multi rinse pipettor 12 can aspirate and discard a portion of the fluid within the cuvette of reaction rotor 6 that was not localized during the localization process.

Multiple rinse cycles can then be performed on the sample within the cuvette of reaction rotor 6. The rinse cycles can be performed using multi rinse pipettor 12 to inject a wash buffer into the cuvette to resuspend the fluo-beads. Another localization step can allow the fluo-beads to collect within the cuvette by the magnets within reaction rotor 6. After about a 90 second fluo-beads collection period, multi rinse pipettor 12 can aspirate and discard a portion of the wash buffer, leaving a substantial portion of the fluo-beads within the cuvette of the reaction rotor 6. Another rinse cycle can then occur using multi rinse pipettor 12 to again inject wash buffer into the cuvette and allow the fluo-beads to resuspend. Another fluo-bead localization process can utilize the magnets within the reaction rotor 6 to localize the fluo-beads from the rest of the sample. Finally, the multi rinse pipettor 12 can aspirate a portion of the sample that was not localized by the localization process.

At this point, R1 pipettor 4 can aspirate a conjugate contained in a conjugate cuvette within reagent rotor 14. R1 pipettor 4 can then inject the previously aspirated conjugate into the cuvette of the reaction rotor 6. After incubating the cuvette under controlled time and temperature in reaction rotor 6, multi rinse pipettor 12 can inject a rinse buffer into the cuvette in reaction rotor 6. Another fluo-bead localization cycle can be performed by allowing magnets within reaction rotor 6 to substantially localize the fluo-beads within the cuvette. Multi rinse pipettor 12 can aspirate and discard a portion of the sample within the cuvette that has not been localized during the localization cycle.

Multiple rinse cycles can be performed on the sample within the cuvette of reaction rotor 6. Multi rinse pipettor 12 can inject a wash buffer to resuspend the fluo-beads within the cuvette. Another fluo-bead localization cycle can localize the fluo-beads by locating the cuvette within close proximity to the magnets in reaction rotor 6 over an adequate period of time. After the localization cycle, multi rinse pipettor 12 can aspirate and discard a portion of the sample that was not localized during the localization cycle. Another wash cycle can then occur by using multi rinse pipettor 12 to inject the wash buffer to resuspend the fluo-beads. Another localization cycle can utilize the magnets within reaction rotor 6 to localize the fluo-beads within the cuvette. After the localization process, multi rinse pipettor 12 can again aspirate and discard a portion of the sample that was not localized during the localization cycle.

At this point, R2 pipettor 22 can aspirate a portion of a first substrate and a second substrate from reagent rotor 14 and inject the substrates into the mixed substrate container 24 creating a mixed substrate sample. R2 pipettor 22 can then aspirate the mixed substrate sample from the mixed substrate container 24 and inject the mixed substrate sample into the cuvette of the reaction rotor 6, resuspending the fluo-bead with the mixed substrate sample. The sample is then incubated for a period of time. The sample in the cuvette of reaction rotor 6 can then be aspirated by optics pipettor 8 and placed in optics box 10. After optics box 10 makes fluorescence and luminescence optical observations, the sample is discarded and the multi rinse pipettor rinses the cuvettes of reaction rotor 6 in preparation for the next test.

For the above steps to be possible, a capture reagent must be bound to the fluo-beads within a cuvette in reaction rotor 6 to create a single solid phase that is then combined with a patient sample. In an embodiment of the present disclosure, a user of automated immunochemistry analyzer 1 can customize a solid phase on the fly with several different capture reagents of the user's choosing. This customizable feature is advantageous because it improves the efficiency and timing to test a patient sample for multiple allergens.

In an embodiment, automated immunochemistry analyzer 1 can include a graphical user interface ("GUI") 30 and a logic implementer 32 that work together to allow a user to customize a solid phase. GUI 30 and logic implementer 32 can accompany or be a part of automated immunochemistry analyzer 1, or can be located remotely from automated immunochemistry analyzer 1 and communicate with automated immunochemistry analyzer 1 via a wireless or wired data connection.

Figure 2:
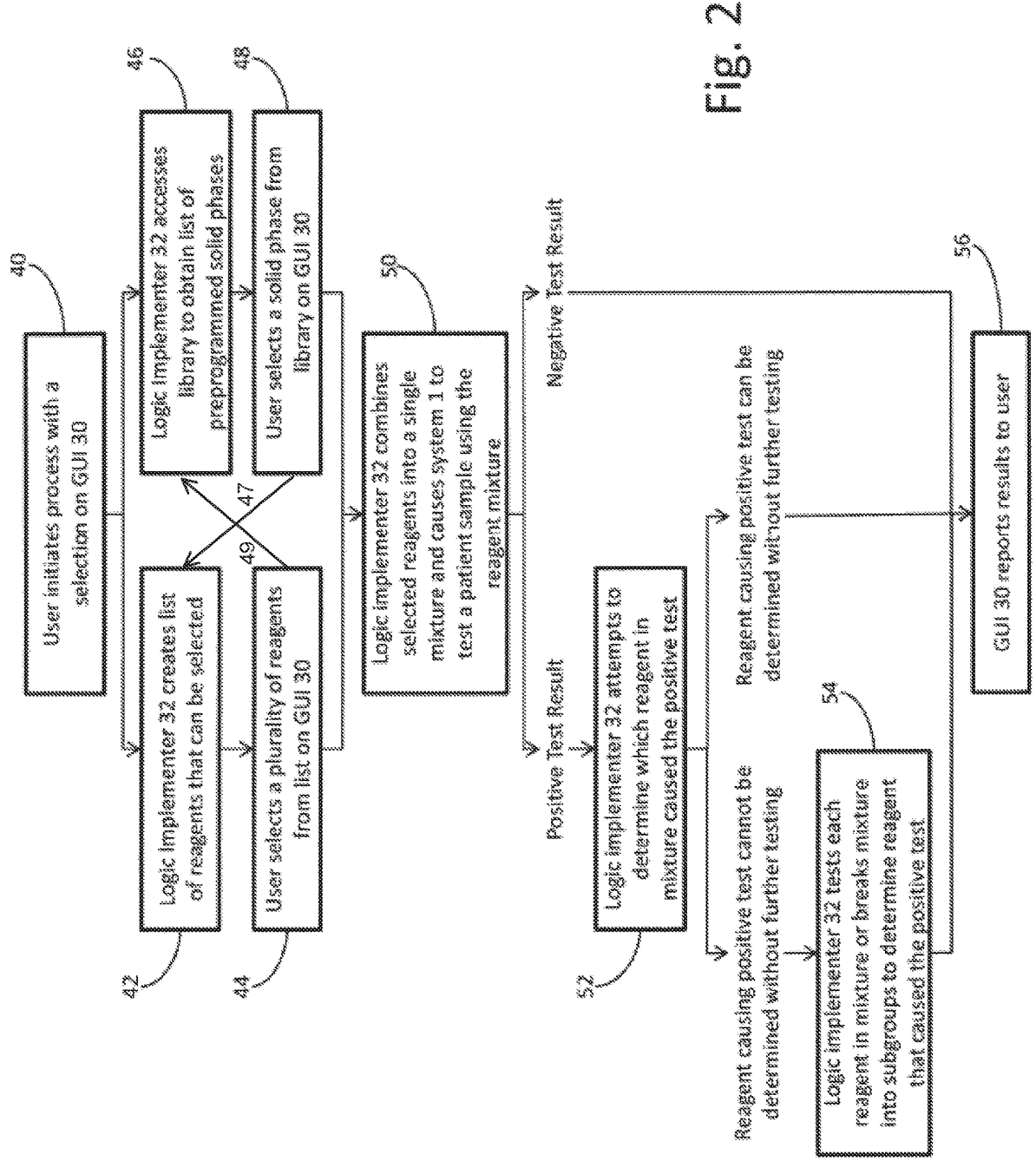
FIG. 2 is a schematic illustration of an embodiment of a process for performing a diagnostic assay according to the present disclosure.

FIG. 2 illustrates a flow chart of a process that uses GUI 30 and logic implementer 32 to allow a user to create a single solid phase that tests a patient sample for multiple allergens. Beginning at step 40, a user initiates the process by instructing GUI 30 that the user wishes to customize a single solid phase with multiple capture reagents. The user can instruct GUI 30 to create a single solid phase for a single patient sample or for multiple patient samples. If the user has previously customized solid phases and saved those solid phases to logic implementer 32, the user can also be presented with the option of recalling a previously customized solid phase from a library of preprogrammed customized solid phases that automated immunochemistry analyzer 1 is capable of creating on the fly based on the capture reagents available to automated immunochemistry analyzer 1. If the user wishes to create a newly customized solid phase, logic implementer 32 proceeds to steps 42 and 44. If the user wishes to access a library of preprogrammed customized solid phases, then the logic implementer 32 proceeds to steps 46 and 48.

At step 42, GUI 30 presents the user with a series of options based on the capture reagents that are available for use within reagent rotor 14. The series of options are provided to GUI 30 by logic implementer 32, which stores information on each of the capture reagents that are available for use within reagent rotor 14. The stored information can include, for example, the name of the capture reagent, the amount of capture reagent currently held by reagent rotor 14, and cross-reactivity interference information on each capture reagent. The stored information can also include a class (e.g., allergy) and subclass (e.g., grass, mold, environmentals, etc.) for each capture reagent. Using the stored information, logic implementer 32 can determine every combination of capture reagents that can be created by automated immunochemistry analyzer 1.

Using the class and subclass of each capture reagent, GUI 30 can present the user with suggested combinations of capture reagents to test. In an embodiment, GUI 30 presents the user with a list of symptoms, from which the user can select one or more symptoms. Based on the selected symptom, GUI 30 can then present the user with a suggested combination of capture reagents. For example, one symptom could be that of an allergic reaction when drinking wine. If the user selected this symptom, GUI 30 could suggest a combination of capture reagents that test for allergic reactions to grapes, yeast, tartaric acid, and other wine ingredients. Other symptoms could include, for example, symptoms related to different autoimmune disorders.

The series of options provided to GUI 30 by logic implementer 32 can be narrowed by logic implementer 32 for a variety of reasons. For example, if the user wishes to create a solid phase to test with multiple patient samples, but reagent rotor 14 does not have enough of a capture reagent stored to create enough solid phase to test each of the samples, logic implementer 32 can either remove that capture reagent as an option, instruct the user as to the deficiency with the capture reagent, or add more of the capture reagent to reagent rotor 14.

Figure 3C:
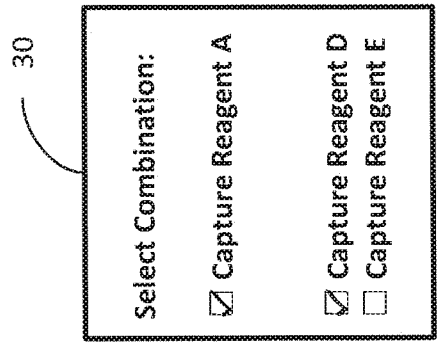
FIG. 3A to 3C illustrate an embodiment of a graphical user interface that can be used with the process of FIG. 2.
Figure 3B:
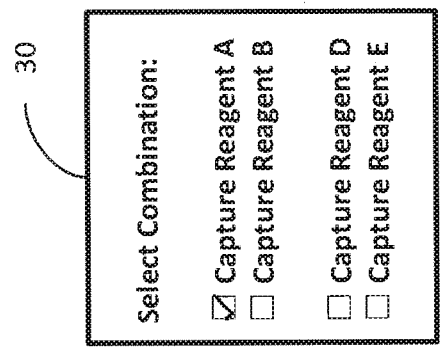
Figure 3A:
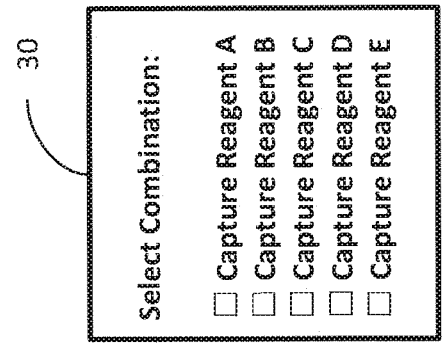

Logic implementer can also determine whether certain capture reagents cannot be combined with other capture reagents, or can place a limit on the total number of capture reagents that can be combined. FIGS. 3A to 3C illustrate an example embodiment of GUI 30, in which the user is presented with five possible capture reagents that are stored in reagent rotor 14. Those of ordinary skill in the art will recognize that more than five capture reagents will be stored in reagent rotor 14 in most instances, but the number has been reduced in the present example for simplicity. In FIG. 3A, the user can click on any one of the five individual capture reagents to add the capture reagent to a combination solid phase. In FIG. 3B, the user has chosen to add Capture Reagent A to the solid phase. When the user makes the selection of Capture Reagent A, however, logic implementer 32 determines that Capture Reagent A and Capture Reagent C cannot be combined, so logic implementer 32 removes Capture Reagent C from the list of remaining options, and Capture Reagent C remains removed from the remaining options unless the user deselects Capture Reagent A. In FIG. 3C, the user has chosen to mix Capture Reagent D with Capture Reagent A. As before, logic implementer 32 then determines that Capture Reagent B is not compatible with Capture Reagent D, so logic implementer 32 removes Capture Reagent B from the list of remaining options, and Capture Reagent B remains removed from the remaining options unless the user deselects Capture Reagent D. In an alternative embodiment, logic implementer 32 removes Capture Reagent B in FIG. 3C because although Capture Reagent B can be compatible with Capture Reagent D, Capture Reagent B is not compatible with the combination of Capture Reagent A and Capture Reagent D.

Logic implementer 32 can therefore continuously reassess the potential options available to the user as the user makes selections, and update GUI 30 with new information. In an alternative embodiment to FIGS. 3A to 3C, the user can be presented with all five options and the logic implementer can wait until after the user has selected the desired capture reagents to determine if the selected capture reagents are compatible. Logic implementer 32 can also be programmed to suggest alternative capture reagents to the user if the user chooses a combination that cannot be created by automated immunochemistry analyzer 1.

In step 44 of FIG. 2, the user has individually selected each capture reagent to be added to a combination. The user therefore finalizes the selected combination, and logic implementer 32 then determines where each of the selected capture reagents is located within reagent rotor 14. Logic implementer 32 can then dispense the appropriate amount of fluo-beads into a cuvette located within the reaction rotor 6, and then control R1 pipettor 4 and reagent rotor 14 to cause R1 pipettor 4 to aspirate each of the individually selected capture reagents from reagent rotor 14 and inject the capture reagents into the cuvette located in reaction rotor 6.

If the user selects at step 40 to access a library of preprogrammed customized solid phases, then the process proceeds from step 40 to step 46, where logic implementer 32 provides GUI 30 with a list of previously stored combinations. In an embodiment, the user at step 44 can save a selected combination to the library for later access by the logic implementer. Alternatively, the stored combinations can be programmed before the user initiates automated immunochemistry analyzer 1, or can be downloaded to automated immunochemistry analyzer 1 via a wireless or wired data connection. Logic implementer 32 can also narrow the selections from the library that are available for selection by the user based on, for example, whether the user exhibits a particular symptom, whether a capture reagent of a combination is available to add to a mixture at the time of selection, or whether an amount of an available capture reagent is enough for the selected test. At step 48, the user makes a selection from the list provided by logic implementer 32, so that logic implementer 32 can then dispense the appropriate amount of fluo-beads into a cuvette located within the reaction rotor 6, and then control R1 pipettor 4 and reagent rotor 14 to cause R1 pipettor 4 to aspirate each capture reagent of the selected combination from reagent rotor 14 and inject the capture reagents into the cuvette located in reaction rotor 6.

In some embodiments, step 47 and/or 49 can be implemented. If step 47 is implemented, after a user selects options at step 44, she can then access previously stored lists. This can be in the form of suggested additional tests based on previously similar lists or can be a list suggested by the system as an alternative or addition to what has been chosen. If step 49 is implemented, after a user access previously stored lists and solid phase form at steps 46 and 48, she can then selects options at step 44. This can allow a user to customize a previously stored list.

In step 50 of FIG. 2, the combination solid phase is combined with a patient sample and incubated, bound and tested as described above by performing several wash steps, adding the conjugate and substrate, and then aspirating the patient sample into optics pipettor 8 so that optics box 10 can take fluorescence and luminescence measurements. As understood by those of skill in the art, a positive result determined by optics box 10 for a mixture of capture reagents indicates a positive result for at least one of the capture reagents in the mixture. For example, a positive test with respect to a mixture containing Capture Reagent A, Capture Reagent B and Capture Reagent C would indicate a positive test for at least one of Capture Reagent A, Capture Reagent B and Capture Reagent C. In this case, however, it may not be possible to determine which one or more of Capture Reagent A, Capture Reagent B and Capture Reagent C caused the positive test. On the other hand, a negative result for a mixture of Capture Reagent A, Capture Reagent B and Capture Reagent C conclusively indicates that the patient sample did not test positive for any one of Capture Reagent A, Capture Reagent B and Capture Reagent C.

Logic implementer 32 can therefore end the test if there is a negative result for the optical analysis of the patient sample at step 50. That is, if logic implementer 32 has determined that the mixture of capture reagents yielded a negative result at step 50, logic implementer 32 can then proceed to step 56 and report to the user via GUI 30 or another mechanism that the patient sample tested negative for each of the capture reagents in the selected mixture.

If the mixture tested positive at step 50, however, logic implementer 32 can proceed to step 52. At step 52, logic implementer attempts to determine whether the positive result can be attributed to a particular capture reagent within the mixture, or whether any particular capture reagent in the mixture can be ruled out as causing the positive result as shown for example at FIG. 6 below. If logic implementer 32 can conclusively determine that each capture reagent of the combination either caused the positive result or could not have caused the positive result, logic implementer 32 can then proceed to step 56 and report to the user via GUI 30 or another reporting mechanism the results for each capture reagent of the combination.

If logic implementer 32 cannot conclusively determine that any one capture reagent in the mixture caused the positive result and that the rest of the capture reagents in the mixture can be eliminated, logic implementer 32 proceeds to step 54. At step 54, logic implementer can either break down the capture reagents into subgroups, or test each individual capture reagent separately, depending on how many capture reagents are in the combination or how many capture reagents could have yielded the positive result. Once logic implementer performs additional testing of the capture reagents and determines whether each capture reagent results in a positive or negative test, logic implementer 32 can then proceed to step 56 and report to the user via GUI 30 or another reporting mechanism the results for each capture reagent of the combination. In an alternative embodiment, logic implementer can skip steps 52 and 54 and simply report to the user via GUI 30 or another reporting mechanism that the patient sample tested positive for at least one of the capture reagents in the mixture.

Figure 4A:
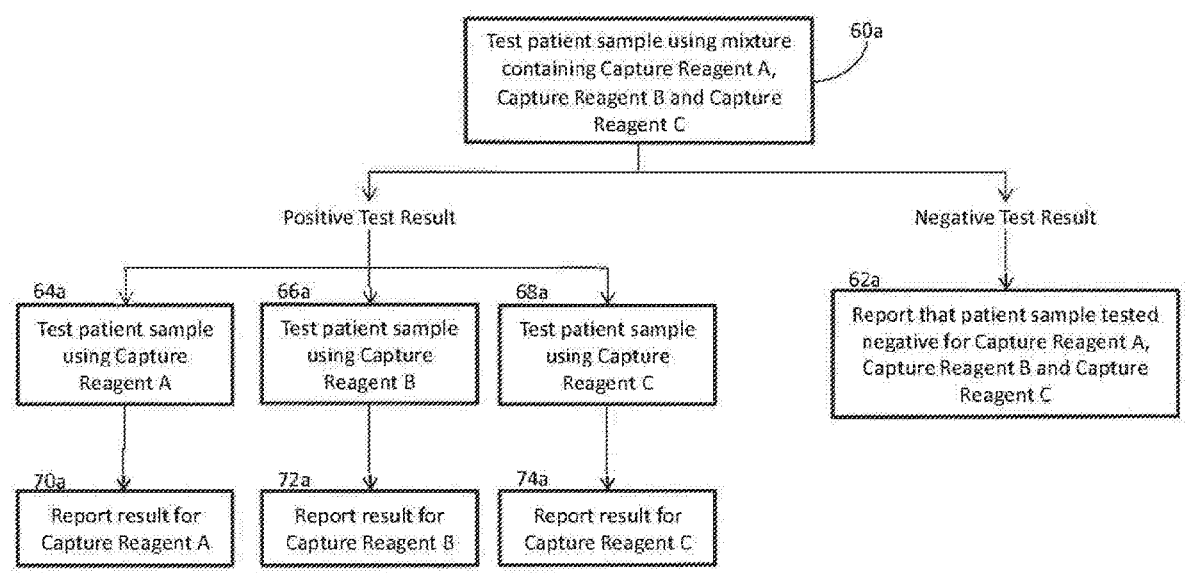
FIGS. 4A and 4B are schematic illustrations of an embodiment of a process for performing a diagnostic assay according to the present disclosure.

FIG. 4A is a flow chart illustrating a simple example of how logic implementer 32 can perform a test of Capture Reagent A, Capture Reagent B and Capture Reagent C. As illustrated, logic implementer 32 begins at step 60a by testing a mixture of Capture Reagent A, Capture Reagent B and Capture Reagent C. If the mixture yields a negative result, then logic implementer can conclusively report at step 62a that the patient sample tested negative for each of Capture Reagent A, Capture Reagent B and Capture Reagent C. If the initial test yields a negative result, only one test is required to report on three different reagents.

If the mixture yields a positive result, then logic implementer at steps 64a, 66a and 68a separately tests each of Capture Reagent A, Capture Reagent B and Capture Reagent C. Logic implementer can then report at steps 70a, 72a and 74a the results for each of Capture Reagent A, Capture Reagent B and Capture Reagent C.

Figure 4B:
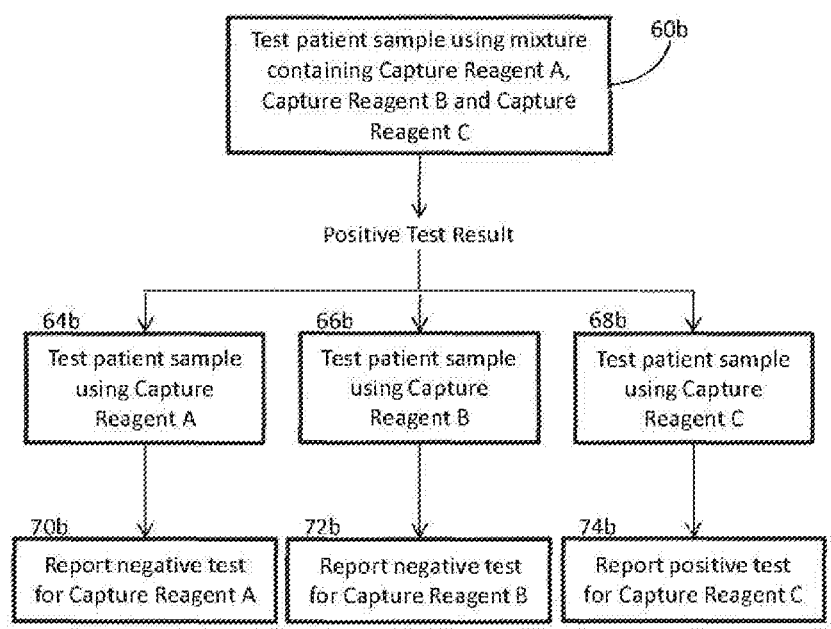

FIG. 4B shows an example of how the testing of FIG. 4A would proceed if only Capture Reagent C tested positive for a particular patient sample. At step 60b, the test yields a positive result for the mixture of Capture Reagent A, Capture Reagent B and Capture Reagent C. Logic implementer 32 therefore separately tests each of Capture Reagent A, Capture Reagent B and Capture Reagent C at steps 64b, 66b and 68b, respectively. At steps 64b and 66b, logic implementer 32 determines that Capture Reagent A and Capture Reagent B yield negative results, which are reported to the user at steps 70b and 72b. At step 68b, logic implementer 32 determines that Capture Reagent C yields a positive result, which is reported to the user at step 74b.

It should be apparent from FIG. 4B that logic implementer 32 ran four separate tests (60b, 64b, 66b, 68b) to determine that the sample tested positive for Capture Reagent C, whereas only three tests would be necessary if each of Capture Reagent A, Capture Reagent B and Capture Reagent C was tested separately from the beginning. It should be understood, however, that the tests are being run for hundreds or thousands of samples, and that every negative test of a three reagent mixture requires only one test (versus three individual tests) to determine that the patient sample tests negatively for each of the three capture reagents. As the number of patient samples increases, the number of total tests decreases significantly. For example, if one hundred patient samples are tested for three different reagents using the example in FIG. 4A, and half of those tests yield a negative result for all three reagents, then the average number of tests per sample would decrease to 2.5 (as opposed to 3 tests per sample if each capture reagent is tested separately) (50*1+50*4=250; 250/100=2.5). Thus, in this example, the total number of tests run for the one hundred patient samples is cut from 300 (with individual testing) to 250 (with mixture testing according to the present disclosure).

In some embodiments described herein, the number of tests run using mixture testing can be reduced by more than about 5%, more than about 10%, more than about 15%, more than about 20%, between about 5% and about 20%, between about 10% and about 20%, between about 15% and about 20%, between about 5% and about 15%, or between about 5% and about 30%.

Figure 5A:
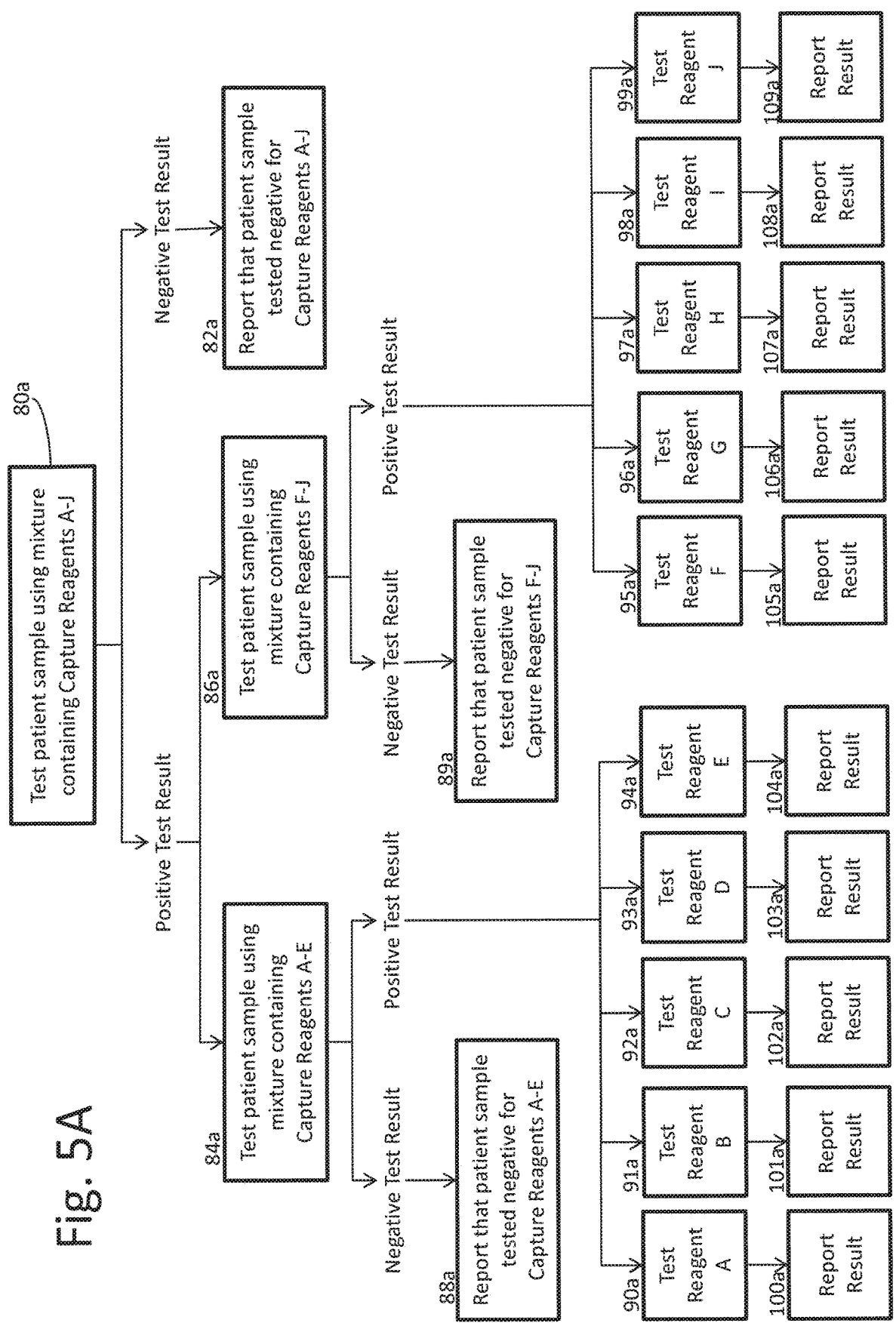
FIGS. 5A and 5B are schematic illustrations of an embodiment of a process for performing a diagnostic assay according to the present disclosure.

The reduction of the total number of tests is even more significant as the number of capture reagents tested is increased. FIG. 5A shows another example of a more complicated scheme in which logic implementer 32 breaks down a ten reagent mixture into subgroups to determine the cause of a positive result. Similar to above, if the ten reagent mixture yields a negative result, then logic implementer 32 can conclusively report that the patient sample tested negative for each of Capture Reagents A-J. If the ten reagent mixture yields a positive result, then logic implementer 32 proceeds to further testing.

In FIG. 5A, logic implementer 32 begins at step 80a by testing a mixture of Capture Reagents A-J. If the mixture yields a negative result, then logic implementer 32 can conclusively report at step 82a that the patient sample tested negative for each of Capture Reagents A-J. If the initial test yields a negative result, only one test is required to report on ten different reagents.

If the test at step 80 yields a positive result, logic implementer 32 moves on to steps 84 a and 86 a, where the logic implementer 32 breaks the ten capture reagents into two subgroups with five reagents in each group. Logic implementer 32 then tests each of the two subgroups, and if either subgroup yields a negative test result, logic implementer 32 can respectively move on to step 88 a or 89 a and report that the live capture reagents in the subgroup each yield a negative result. If one or both of the two subgroups yields a positive result, logic implementer 32 can move on to steps 90 *a*-99 *a*, where the capture reagents are separately, tested. Logic implementer 32 can then report the results at steps 100 *a*-109 *a*.

Figure 5B:
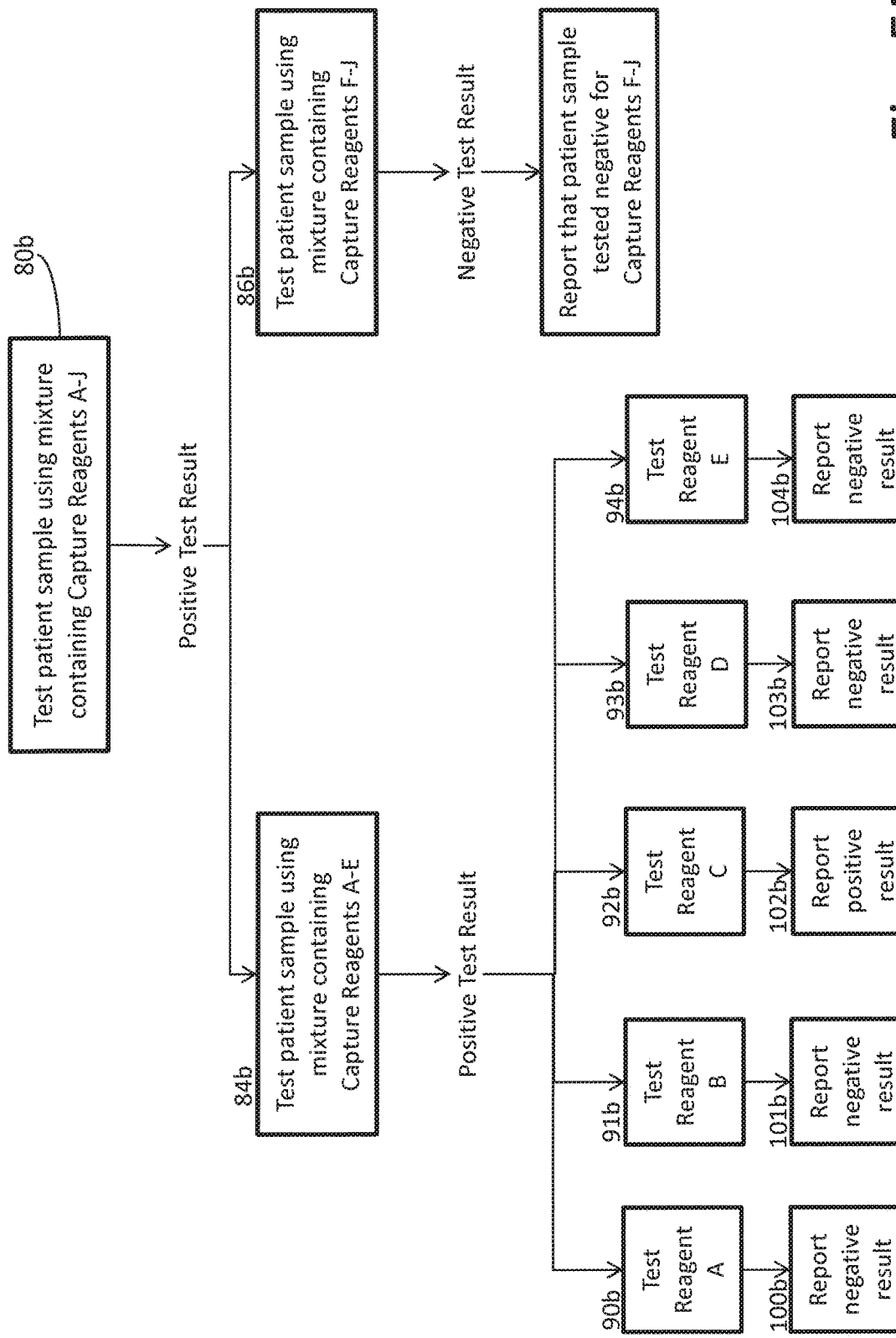

FIG. 5B shows an example of how the testing of FIG. 5A would proceed if only Capture Reagent C tested positive for a particular patient sample. At step 80*b*, the test yields a positive result for the mixture of Capture Reagents A-J. Logic implementer 32 therefore separates Capture Reagents A-J into a first subgroup with Capture Reagents A-E and a second subgroup with Capture Reagents F-J, and separately tests the first subgroup and the second subgroup at steps 84*b* and 86*b*, respectively.

At step 86*b*, logic implementer 32 determines that the second subgroup with Capture Reagents F-J yields a negative result. Logic implementer 32 can therefore conclusively determine that none of Capture Reagents F-J caused the positive result at step 80*b*, and logic implementer 32 can report the negative result for each of Capture Reagents F-J at step 89*b*.

At step 84*b*, logic implementer 32 determines that the first subgroup with Capture Reagents A-E yields a positive result. Logic implementer 32 can then break the first subgroup into additional subgroups or test each of the capture reagents separately. In the example shown, logic implementer 32 has tested each the capture reagents in the first subgroup separately, and has determined at step 92*b* that Capture Reagent C caused the initial positive result at step 80*b*. The positive result for Capture Reagent C, as well as the negative results for each of the other capture reagents, are then reported to the user at steps 89*b* and 100*b*-104*b*.

In the example of FIG. 5B, logic implementer 32 runs a total of eight tests (80*b*, 84*b*, 86*b*, 90*b*, 91*b*, 92*b*, 93*b*, 94*b*) to determine that the sample tested positive for Capture Reagent C, whereas ten tests would be necessary if each of Capture Reagents A-J was tested separately from the beginning. In comparison with the example of FIG. 4, FIG. 5 demonstrates that as the number of capture reagents in the initial mixture increases, the relative number of tests performed decreases. In the example of FIG. 5B, if one hundred patient sample were tested for ten different reagents, and half of those tests yielded a positive result for one reagent, then the average number of tests per sample would decrease to 4.5 (as opposed to 10 tests per sample if each capture reagent is tested separately) (50*1+50*8=450; 450/100=4.5). Thus, in this example, the total number of tests run for the one hundred patient samples is cut from 1000 (with individual testing) to 450 (with mixture testing according to the present disclosure).

Figure 6:
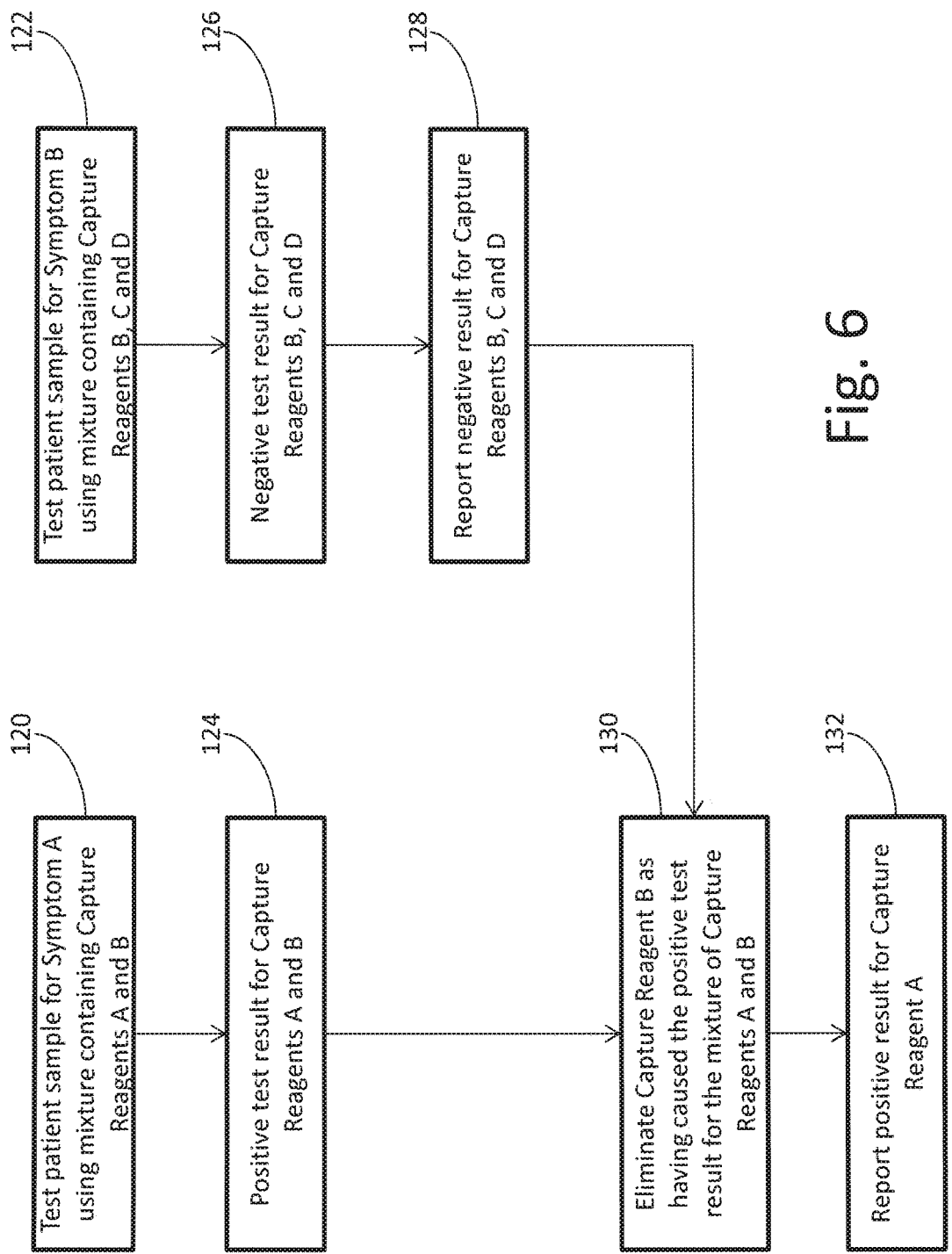
FIG. 6 is a schematic illustration of an embodiment of a process for performing a diagnostic assay according to the present disclosure.

FIG. 6 shows one example embodiment of how logic implementer 32 can eliminate a capture reagent as having caused a positive test result, without having to retest the particular capture reagent. In FIG. 6, logic implementer 32 initiates two separate tests. At step 120, logic implementer 32 initiates a test for Symptom A by testing a mixture of Capture Reagents A and B, and at step 122 logic implementer 32 initiates a test for Symptom B by testing a mixture of Capture Reagents B, C and D. At step 124, logic implementer determines that the mixture of Capture Reagents A and B yielded a positive result, which could be attributed to Capture Reagent A, Capture Reagent B, or both of Capture Reagents A and B. At step 126, however, logic implementer determines that the mixture of Capture Reagents B, C and D yielded a negative result, meaning that the patient sample tested negative for each of Capture Reagents B, C and D, which logic implementer can report to the user via GUI 30 or another mechanism at step 128. At step 130, logic implementer combines the tests for Symptom A and Symptom B, and determines that Capture Reagent B could not have caused the positive result for the mixture of Capture Reagents A and B because the patient sample tested negative for Capture Reagent B and step 126. Logic implementer 32 can therefore report to the user at step 132 that Capture Reagent A caused the positive result of the test of the mixture of Capture Reagents A and B.

Figure 7:
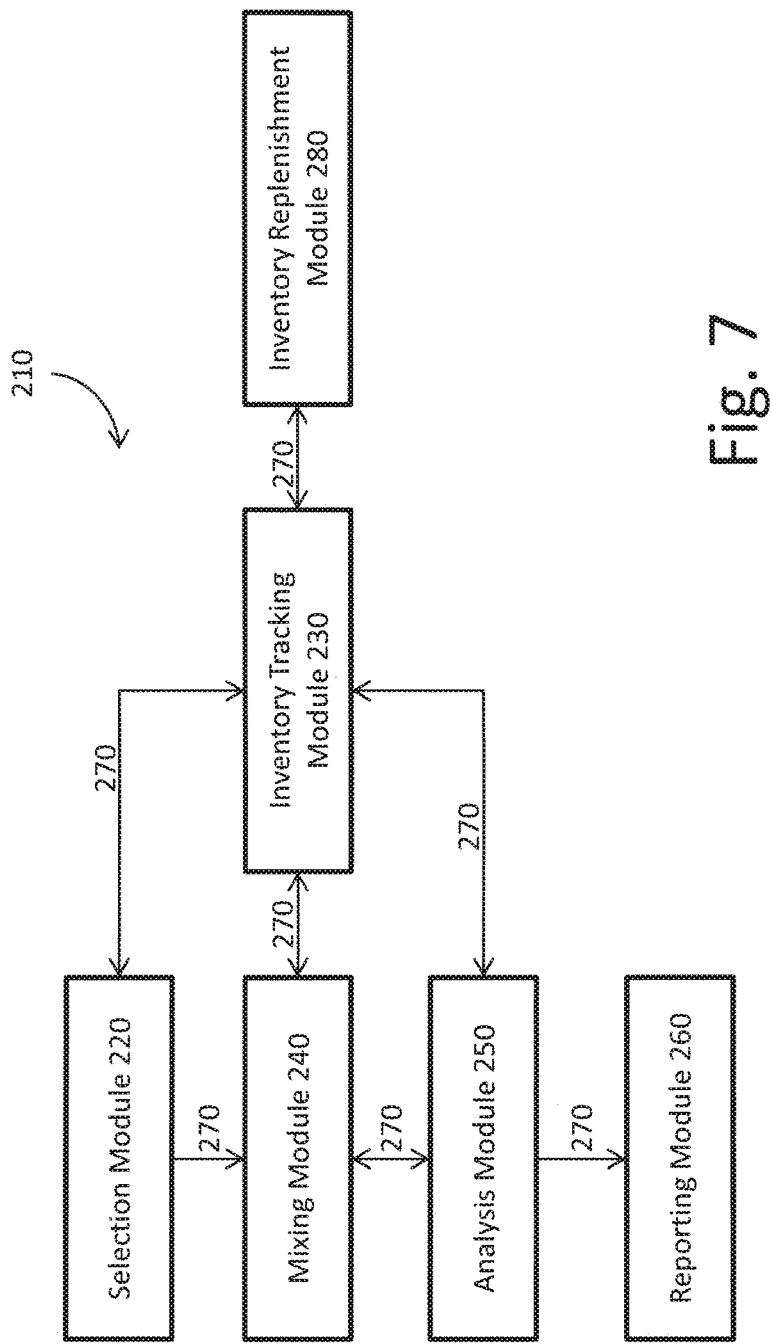
FIG. 7 is a schematic illustration of an embodiment of a system that can be controlled to perform the processes of FIGS. 2 to 6.

FIG. 7 illustrates an embodiment of a system 210 with a plurality of optimization modules that are controlled by logic implementer 32 to perform the above process. In the illustrated embodiment, system 210 includes a selection module 220, an inventory tracking module 230, a mixing module 240, and analysis module 250, a reporting module 260, a communications module 270 and an inventory replenishment module 280. Those of ordinary skill in the art will recognize that more or less modules can be utilized according to the present disclosure.

Selection module 220 initiates the process illustrated at FIGS. 2 to 5, for example, when a user turns on automated immunochemistry analyzer 1 or indicates via GUI 30 that a new test is to be run using automated immunochemistry analyzer 1. In an embodiment, selection module 220 allows the user to select via GUI 30 one or more patient samples to use for one or more new tests. The selection of one or more patient samples can be performed at the initiation or later in the process. In an alternative embodiment, patient data can be downloaded to selection module 220 via communications module 270, which can include a wireless network or a wired connection. In another embodiment, the selection of one or more patient samples can occur via the downloaded data.

Once the process has been initiated, selection module 220 communicates to inventory tracking module 230 via communications module 270 that a new test is to be run. Inventory tracking module 230 keeps track of the reagents and/or patient samples that are available for use by automated immunochemistry analyzer 1, for example, by accessing stored information on each of the capture reagents that are available within reagent rotor 14 and/or each of the patient samples that are stored in sample rotor 18. The stored information can be programmed by a user when new reagents and/or patient samples are added to automated immunochemistry analyzer 1, can be scanned into the system prior to initiation of the test using, for example, a machine-readable data scanner such as a barcode scanner, or can be generated by the inventory tracking module 230 via the machine-readable data scanner at the time that a new test is initiated by selection module 220. The stored information can include, for example, the name of the capture reagent, the amount of capture reagent currently held by reagent rotor 14, cross-reactivity interference information on each capture reagent and/or patient identification or blood sample information. The stored information can also include a class (e.g., allergy) and subclass (e.g., grass, mold, environmentals, etc.) for each capture reagent.

Inventory tracking module 230 can also communicate with an inventory replenishment module 280 if one or more reagents are not available within the reagent rotor 14 but are available for use by automated immunochemistry analyzer 1. In an embodiment, spare capture reagent can be stored outside of reagent rotor 14 and accessed or added to reagent rotor 14 when needed.

Once inventory tracking module 230 has surveyed the available inventory, inventory tracking module 230 communicates the available inventory to selection module 220 via communications module 270. Selection module 220 then organizes the available inventory and presents the available inventory to the user via GUI 30. In an embodiment, selection module 220 presents the user with a series of options based on the capture reagents that are available within reagent rotor 14. The series of options can be a list of available reagents for individual selection. Alternatively, the series of options can be preprogrammed combinations that are available to the user based on the individual reagents that are available. In an embodiment, the preprogrammed combinations are based on a particular symptom exhibited by the patient. For example, if the user has previously customized solid phases and saved those solid phases, the user can be presented with the option of recalling a previously customized solid phase from a library of preprogrammed customized solid phases that the automated immunochemistry analyzer 1 is capable of creating on the fly based on the available inventory.

Selection module 220 then allows the user to individually select capture reagents to combine, to select a combination of capture reagents, and/or to select patient samples for testing via GUI 30. The user can also be presented with the option of saving a selected combination of capture reagents that can be recalled for subsequent tests.

Once a selection of a combination of capture reagents has been made, selection module 220 communicates the selected combination to mixing module 240 via communications module 270. Mixing module 140 then accesses reagent rotor 14 via R1 pipettor 4 and causes each selected capture reagent to be added to a cuvette within reaction rotor 6.

In an embodiment, mixing module 240 communicates with inventory tracking module 230 via communications module 270, before the capture reagents are mixed, to communicate the selected combination to inventory tracking module 230. Inventory tracking module 230 then confirms that each of the selected capture reagents is available for use and sends mixing module 240 the exact location of each of the selected capture reagents within reagent rotor 14. If the capture reagents need replenishment by inventory replenishment module 280, then inventory tracking module 230 communicates with inventory replenishment module 280 so that the needed capture reagents are added to reagent rotor 14, and then communicates the location of the newly added capture reagents to mixing module 240. Once mixing module 240 knows the location of each individual capture reagent of the selected combination, mixing module 240 can cause R1 pipettor 4 to separately aspirate each capture reagent and inject each capture reagent into a cuvette in reaction rotor 6. In an alternative embodiment, the location of each capture reagent of the selected combination in reagent rotor 14 can be communicated to mixing module 240 by selection module 220 without mixing module 240 having to communicate with inventory tracking module 230.

Once the selected capture reagents have been mixed and incubated so that the analytes of interest in the patient's blood sample are bound to the capture reagent that has in turn been bound to the surface of a paramagnetic particle, analysis module 250 causes the patient sample to be tested through the addition of conjugates and substrates for fluorescence and luminescence within optics box 10, and then analyzes the results to determine whether the test yielded a positive or negative result. As described above, a positive result determined by optics box 10 for a mixture of capture reagents indicates a positive result for at least one of the capture reagents in the mixture, whereas a negative result determined by optics box 10 for a mixture of capture reagents conclusively indicates that the patient sample did not test positive for any one of the capture reagents in the mixture. Analysis module 250 therefore analyzes the results of the test to determine whether it can conclusively determine the results of the test with respect to each capture reagent in the mixture.

If the test result is negative for the mixture, analysis module 250 determines that the patient sample tested negative for each capture reagent in the mixture, and communicates with reporting module 260 via communications module 270 so that reporting module 260 can process the results and report the results to the user via GUI 30 or another reporting mechanism. If the test result is positive for the mixture, analysis module 250 determines whether the positive result can be attributed to a particular capture reagent within the mixture, or whether any particular capture reagent in the mixture can be ruled out as causing the positive result. If analysis module 250 can conclusively determine that each capture reagent of the combination either caused the positive result or could not have caused the positive result, analysis module 250 communicates with reporting module 260 via communications module 270 so that reporting module 260 can process the results and report the results to the user via GUI 30 or another reporting mechanism.

If analysis module 250 cannot conclusively determine that each capture reagent of the combination either caused the positive result or could not have caused the positive result, then analysis module 250 can either break down the mixture of capture reagents into subgroups, or test each individual capture reagent separately, depending on how many capture reagents are in the combination or how many capture reagents could have yielded the positive result. In an embodiment, analysis module 250 communicates with inventory tracking module 230 while breaking down the mixture into subgroups or individual capture reagents to ensure that that there is enough inventory for the further testing. In another embodiment, analysis module 250 breaks down the mixture of capture reagents based on the remaining inventory. For example, if there is only enough of a capture reagent to run one more test, analysis module 250 may choose to test that capture reagent individually rather than risk another inconclusive test.

Once analysis module 250 has determined how the subsequent testing is to be performed, analysis module 250 communicates the subsequent testing to mixing module 240 via communications module 270 so that mixing module 240 can prepare a new mixture or new individual samples. Mixing module 240 can again communicate with inventory tracking module 230 via communications module 270 to communicate the subsequent testing to inventory tracking module 230, confirm that each of the necessary capture reagents is available for use, and receive the exact location of each of the selected capture reagents for aspiration by R1 pipettor 4. Once the selected capture reagents have been mixed and incubated so that the analytes of interest in the patient's blood sample are bound to the capture reagent that has in turn been bound to the surface of a paramagnetic particle, analysis module 250 again causes the patient sample to be tested through the addition of conjugates and substrates for fluorescence and luminescence within optics box 10, and then analyzes the results to determine whether the test yielded a positive or negative result. Analysis module 250 then either determines that additional testing should take place or that reporting module 260 can process the final results and report the results to the user via GUI 30 or another reporting mechanism.

Disclosed herein are methods and systems for testing of patient samples with combinations of capture reagents. In alternative embodiments, the combination includes two to twelve capture reagents. In other embodiments, the combination includes three or more capture reagents, four or more capture reagents, five or more capture reagents, six or more capture reagents. In yet other embodiments, the combination includes three capture reagents, four capture reagents, five capture reagents, six capture reagents, seven capture reagents, eight capture reagents, nine capture reagents, or ten capture reagents.

In some embodiments, the systems described herein can include an auto-reflexing function. The auto-reflexing function uses a processor to access a program stored in memory that if an answer a test comes back positive, the system can alert a user that assays for individual analytes in the sample may be desired. In other embodiments, upon receiving a positive result, the system can automatically assay for individual analytes in the sample. Automatically can me without user intervention. In other embodiments, user intervention may be required prior to running further tests on individual analytes.

In other embodiments, the positive or negative results described herein can be qualitative or quantitative. In some embodiments, results may be a simply positive (e.g., true) or negative (e.g., false) based on pre-determined criterion. In other embodiments, results may be a particular value that is then scaled or determined to be positive or negative depending on pre-determined criterion.

Further, logic steps described herein can be completed by a user or one or more processor that is executing instructions stored in memory.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention claimed is:

1. A system for optically analyzing a patient sample for a plurality of allergens, the system comprising:
   an automated immunochemistry analyzer configured to store a plurality of capture reagents and a plurality of paramagnetic particles;

a user interface configured to allow a selection of a combination of two or more capture reagents from the plurality of capture reagents; and a logic implementer configured to cause the automated immunochemistry analyzer to
  (i) mix together each capture reagent of the combination of two or more capture reagents,
  (ii) bind the mixture of the combination of two or more capture reagents to the paramagnetic particles,
  (iii) bind analyte molecules from the patient sample to the bound mixture of the combination of two or more capture reagents,
  (iv) optically analyze the bound analyte molecules from the patient sample,
  (v) responsive to the optical analysis of the bound analyte molecules being indicative of a negative result related to the plurality of allergens, provide an indication of the negative result, and
  (vi) responsive to the optical analysis of the bound analyte molecules being indicative of a positive result related to the plurality of allergens:
    create automatically a first subgroup by binding a first sub-combination of the two or more capture reagents to the paramagnetic particles,
    create automatically a second subgroup by binding a second sub-combination of the two or more capture reagents to the paramagnetic particles, the second sub-combination being different from the first sub-combination,
    bind the first subgroup to a first set of analyte molecules from the patient sample,
    bind the second subgroup to a second set of analyte molecules from the patient sample,
    optically analyze the first and second subgroups, and
    identify which of the capture reagents caused the positive result based on which of the first and second subgroups produces a second positive result.

2. The system of claim 1, wherein the combination of two or more capture reagents is a combination of three or more capture reagents.

3. The system of claim 1, wherein the logic implementer is configured to limit the number of capture reagents that the user interface allows for selection.

4. The system of claim 3, wherein the logic implementer is configured to limit the number of capture reagents that the user interface allows for selection based on the availability of the capture reagents within the automated immunochemistry analyzer.

5. The system of claim 1, wherein the logic implementer is configured to store a plurality of preprogrammed combinations of two or more capture reagents for selection using the user interface or configured to adjust the number of capture reagents that the user interface allows for selection as the selection is being made.

6. The system of claim 5, wherein the plurality of preprogrammed combinations are sorted by a type of symptom exhibited by the patient.

7. The system of claim 1, wherein the selection of the combination of two or more capture reagents is made by individually selecting each of the capture reagents in the combination.

8. The system of claim 1, wherein the first sub-combination of the two or more capture reagents and the second sub-combination of the two or more capture reagents include at least one common capture reagent.

9. A system for optically analyzing a patient sample for a plurality of allergens, the system comprising:
  a plurality of capture reagents;
  a plurality of paramagnetic particles;
  a selection module that allows a selection of a combination of two or more capture reagents from the plurality of capture reagents;
  a mixing module that (i) mixes together each capture reagent of the combination of two or more capture reagents, (ii) binds the mixture of the combination of two or more capture reagents to the paramagnetic particles, and (iii) binds analyte molecules from the patient sample to the bound mixture of the combination of two or more capture reagents;
  an analysis module that optically analyzes the bound analyte molecules from the patient sample for one or more positive or negative result;
  a reporting module which reports the one or more positive or negative result determined by the analysis module; and
  a logic implemented configured to:
    responsive to the optical analysis of the bound analyte molecules being indicative of a negative result, provide an indication of the negative result via the reporting module, and
    responsive to the optical analysis of the bound analyte molecules being indicative of a positive result:
      cause the mixing module to create a first subgroup by binding a first sub-combination of the two or more capture reagents to the paramagnetic particles, and create a second subgroup by binding a second sub-combination of the two or more capture reagents to the paramagnetic particles, the second sub-combination being different from the first sub-combination,
      cause the mixing module to bind the first subgroup to a first set of analyte molecules from the patient sample, and bind the second subgroup to a second set of analyte molecules from the patient sample,
      cause the analysis module to optically analyze the first and second subgroups,
      identify which of the capture reagents caused the positive result based on which of the first and second subgroups produces a second positive result, and
      cause the reporting module to provide an indication of the identified capture reagent that produced the second positive result.

10. The system of claim 9, wherein the combination of two or more capture reagents is a combination of three or more capture reagents.

11. The system of claim 9, which includes an inventory tracking module that stores locations of the plurality of capture reagents and communicates the locations of the plurality of capture reagents to at least one of: (i) the selection module; (ii) the mixing module; and (iii) the analysis module.

12. The system of claim 9, which includes an inventory replenishment module that replenishes the plurality of capture reagents.

13. The system of claim 9, wherein the first sub-combination of the two or more capture reagents and the second sub-combination of the two or more capture reagents include at least one common capture reagent.

14. The system of claim 9, wherein the selection module allows for individual selection of each capture reagent of the combination of two or more capture reagents, or allows for selection of the combination of two or more capture reagents from a plurality of preprogrammed combinations of two or more capture reagents.

15. The system of claim 3, wherein the logic implementer is configured to limit the number of capture reagents that the user interface allows for selection to reduce cross-reactivity interference between the combination of two or more capture reagents.

16. The system of claim 1, wherein the logic implementer is configured to identify the capture reagent of the combination of two or more capture reagents based on a selection at the user interface of a solid phase or a selection of allergen types to be tested.

17. The system of claim 9, wherein the logic implementer is configured to limit the number of capture reagents that the selection module allows for selection.

18. The system of claim 17, wherein the logic implementer is configured to limit the number of capture reagents that the selection module allows for selection based on the availability of the capture reagents within the automated immunochemistry analyzer.

19. The system of claim 17, wherein the logic implementer is configured to limit the number of capture reagents that the selection module allows for selection to reduce cross-reactivity interference between the combination of two or more capture reagents.

20. The system of claim 9, wherein the logic implementer is configured to identify the capture reagent of the combination of two or more capture reagents based on a selection at the selection module of a solid phase or a selection of allergen types to be tested.

* * * * *